(12) United States Patent
Mrzena et al.

(10) Patent No.: US 8,628,684 B2
(45) Date of Patent: Jan. 14, 2014

(54) PROCESS FOR THE PREPARATION OF A POWDER COMPRISING ONE OR MORE DERIVATIVES OF GLYCINE-N,N DIACETIC ACID AND/OR ONE OR MORE DERIVATIVES OF GLUTAMINE-N,N DIACETIC ACID AND METHYLGLYCINE-N,N DIACETIC ACID TRISODIUM SALT POWDER

(75) Inventors: Frank Mrzena, Mutterstadt (DE); Hans-Juergen Kinder, Speyer (DE); Michael Schoenherr, Frankenthal (DE); Gerhard Cox, Bad Duerkheim (DE); Thomas Schmidt, Neustadt (DE); Volker Huett, Hockenheim (DE)

(73) Assignee: BASF SE, Ludwigshafen (DE)

( * ) Notice: Subject to any disclaimer, the term of this patent is extended or adjusted under 35 U.S.C. 154(b) by 92 days.

(21) Appl. No.: 13/318,513

(22) PCT Filed: May 19, 2010

(86) PCT No.: PCT/EP2010/056856
§ 371 (c)(1),
(2), (4) Date: Nov. 2, 2011

(87) PCT Pub. No.: WO2010/133618
PCT Pub. Date: Nov. 25, 2010

(65) Prior Publication Data
US 2012/0046491 A1 Feb. 23, 2012

Related U.S. Application Data

(60) Provisional application No. 61/253,908, filed on Oct. 22, 2009.

(30) Foreign Application Priority Data

May 20, 2009 (EP) .................................... 09160718

(51) Int. Cl.
*C09K 3/00* (2006.01)
*C07C 61/08* (2006.01)

(52) U.S. Cl.
USPC ....................... 252/182.3; 562/507

(58) Field of Classification Search
USPC ....................... 252/182.3; 562/507
See application file for complete search history.

(56) References Cited

U.S. PATENT DOCUMENTS

| 3,932,316 A | 1/1976 | Sagel et al. |
| 5,981,798 A | 11/1999 | Schonherr et al. |
| 2011/0118110 A1 | 5/2011 | Kotrel et al. |

FOREIGN PATENT DOCUMENTS

| EP | 0 845 456 | 6/1998 |
| EP | 1 334 961 | 8/2003 |

OTHER PUBLICATIONS

International Search Report Issued Oct. 1, 2010 in PCT/EP10/056856 Filed May 19, 2010.
U.S. Appl. No. 61/253,911, filed Oct. 22, 2009, Mrzena, et al.
U.S. Appl. No. 13/321,713, filed Nov. 21, 2011, Mrzena, et al.
U.S. Appl. No. 13/242,540, filed Sep. 23, 2011, Blei, et al.

*Primary Examiner* — Johann R Richter
*Assistant Examiner* — Kofi Adzamli
(74) *Attorney, Agent, or Firm* — Oblon, Spivak, McClelland, Maier & Neustadt, L.L.P.

(57) ABSTRACT

A process is proposed for the preparation of a powder comprising one or more derivatives of glycine-N,N-diacetic acid and/or one or more derivatives of glutamine-N,N-diacetic acid with a degree of crystallinity of ≥30%,
starting from an aqueous solution comprising the one or more derivatives of glycine-N,N-diacetic acid and/or the one or more derivatives of glutamine-N,N-diacetic acid in a concentration range from 20 to 60% by weight, based on the total weight of the aqueous solution, where
the aqueous solution is concentrated in a first process step in an evaporator with rotating internals, which are arranged at a distance relative to the inside wall of the evaporator of ≤1% of the diameter of the evaporator, to give a crystal slurry with a solids concentration in the range from 60 to 85% by weight, based on the total weight of the crystal slurry, and where
in a second process step the crystal slurry is left to ripen in a paste bunker and then in a thin-film contact dryer, and where the residence time in the paste bunker and in the thin-film contact dryer is in total ≥15 minutes.

13 Claims, 3 Drawing Sheets

Figure 1:
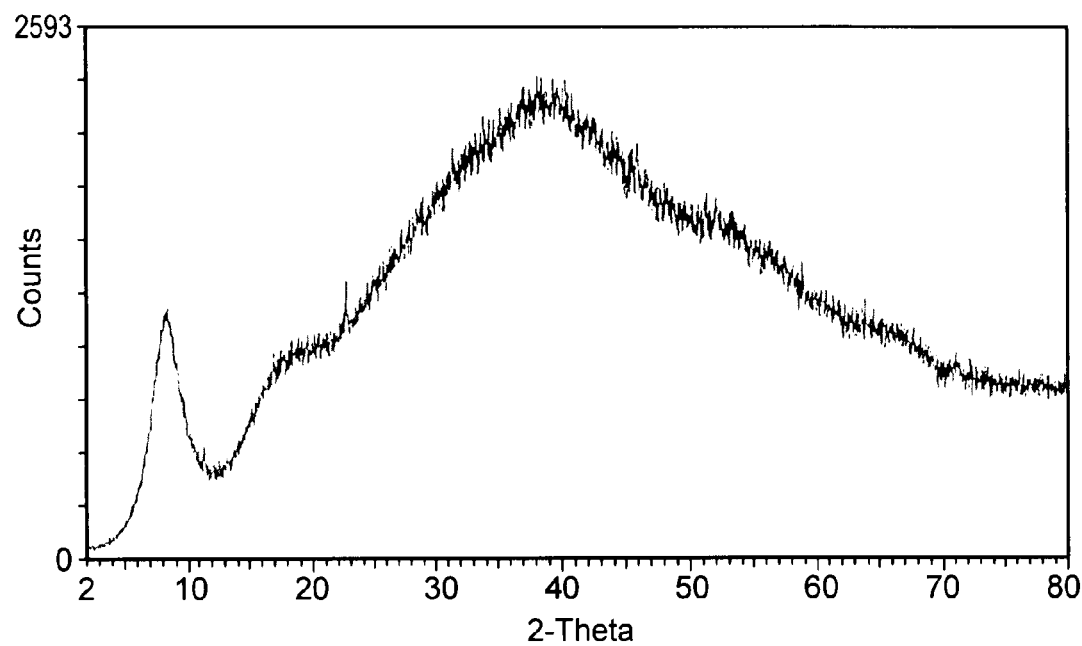
Figure 2:
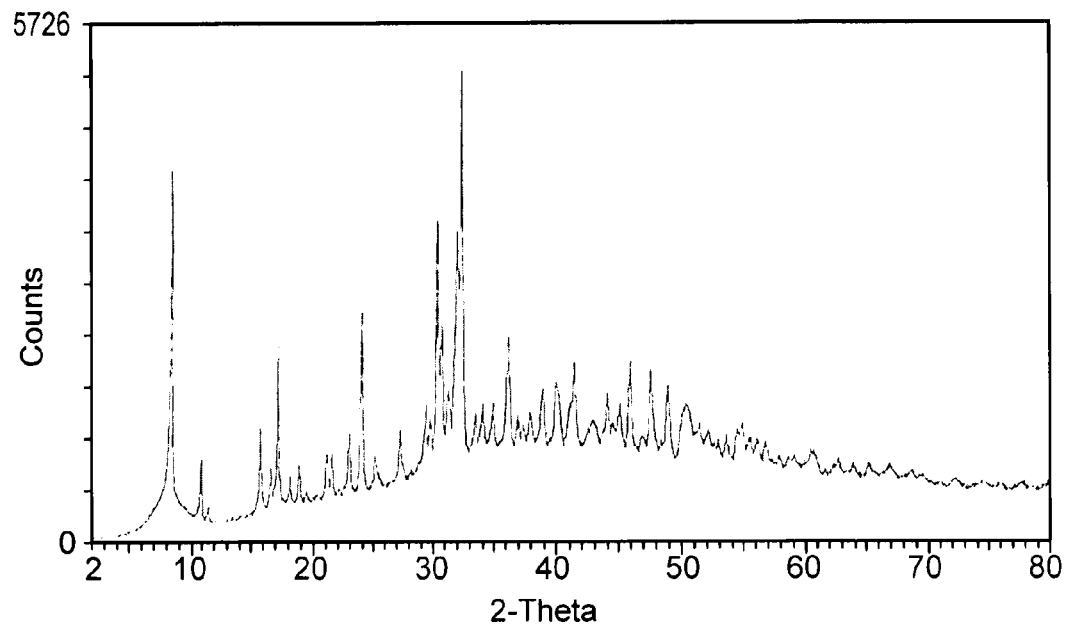
Figure 3:
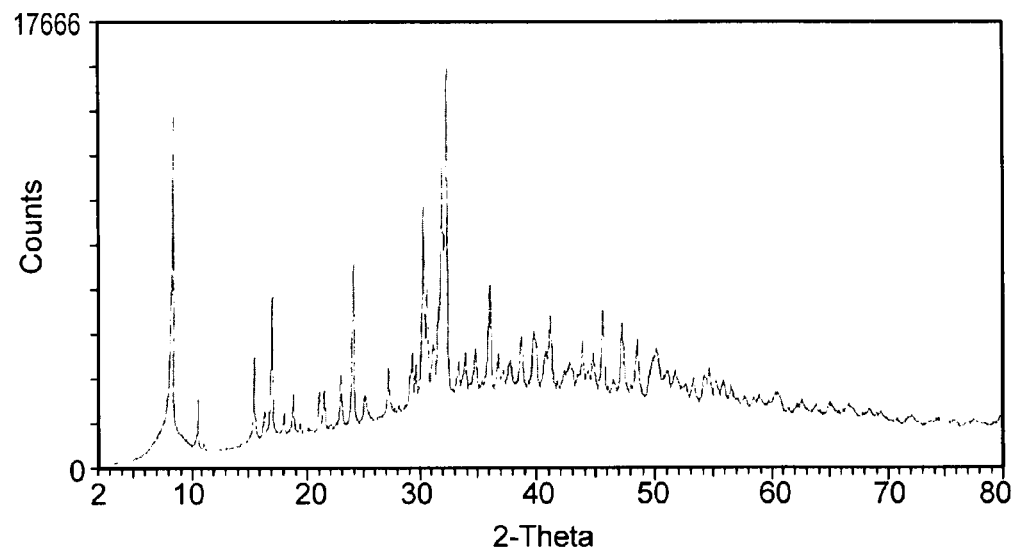

PROCESS FOR THE PREPARATION OF A POWDER COMPRISING ONE OR MORE DERIVATIVES OF GLYCINE-N,N DIACETIC ACID AND/OR ONE OR MORE DERIVATIVES OF GLUTAMINE-N,N DIACETIC ACID AND METHYLGLYCINE-N,N DIACETIC ACID TRISODIUM SALT POWDER

The invention relates to a process for the preparation of a powder comprising one or more derivatives of glycine-N,N-diacetic acid and/or one or more derivatives of glutamine-N,N-diacetic acid and methylglycine-N,N-diacetic acid trisodium salt powder.

Derivatives of glycine-N,N-diacetic acid have complexing properties for alkaline earth metal ions and heavy metal ions and are used in broad sectors of industry e.g. in the detergent and cleaners industry or in the treatment of metal surfaces etc. In many applications, these active components are used as solids with other solids together as mixtures e.g. converted to tablet form and as dishwasher tablets. The preparation of the powders takes place here primarily from aqueous solutions, although this leads to correspondingly complex and uneconomical mass crystallization processes (evaporation and cooling crystallization) since the asymmetrical molecular shape greatly hinders the crystallization.

Consequently, these powders are produced industrially in most cases in spray-drying plants, although this leads to solids with high amorphous fractions. This leads to highly hygroscopic behavior and poor storability and further processability e.g. in tableting presses etc., which is compensated for by aftertreatment in builders for detergents to the addition of benzoic acid (cf. U.S. Pat. No. 3,932,316).

EP-A 08 45 456 describes a process for the preparation of powders of the above complexing agents with increased degree of crystallinity, where in particular starting masses with water fractions in the range from 10-30% are used and preferably crystallization seeds are added. This process leads to predominantly crystalline powders, but, on account of the viscous and pasty phases during the preparation, requires the use of complex mixer-kneader apparatuses in order to contribute to ensuring conversion to the crystalline modifications.

Accordingly, it was an object of the invention to provide a technically simpler process for the provision of powders of the above complexing agents with increased degree of crystallinity.

The solution consists in a process for the preparation of a powder comprising one or more derivatives of glycine-N,N-diacetic acid and/or one or more derivatives of glutamine-N,N-diacetic acid with a degree of crystallinity of ≥30%, starting from an aqueous solution comprising the one or more derivatives of glycine-N,N-diacetic acid and/or the one or more derivatives of glutamine-N,N-diacetic acid in a concentration range from 20 to 60%, based on the total weight of the aqueous solution, where
the aqueous solution is concentrated in a first process step in an evaporator with rotating internals, which are arranged at a distance relative to the inside wall of the evaporator of ≤1% of the diameter of the evaporator, to give a crystal slurry with a solids concentration in the range from 60 to 85% by weight, based on the total weight of the crystal slurry, and where
in a second process step the crystal slurry is left to ripen in a paste bunker and then in a thin-film contact dryer, and where the residence time in the paste bunker and in the thin-film contact dryer is in total ≥15 minutes.

The process starts from aqueous solutions comprising one or more derivatives of glycine-N,N-diacetic acid and/or one or more derivatives of glutamine-N,N-diacetic acid, preferably one or more alkali metal salts of methylglycine-N,N-diacetic acid, referred to below in abbreviated form as MGDA, in a total concentration in the range from about 20 to 60%, based on the total weight of the solution.

Preference is given to using derivatives of glycine-N,N-diacetic acid or of glutamine-N,N-diacetic acid with high purity. The by-products from the synthesis should be present in the lowest possible fractions, in particular the fraction of 2-(carboxymethylamino)propionic acid disodium salt should be <2%, nitrilotriacetic acid trisodium salt <0.5%, iminodiacetic acid disodium salt <2% and sodium hydroxide <2%. In particular, the starting material used is an aqueous solution which comprises the one or more derivatives of glycine-N,N-diacetic acid and/or of glutamine-N,N-diacetic acid in each case in a purity of ≥84%, based on the dry mass.

Preference is given to using one or more derivatives of glycine-N,N-diacetic acid and/or one or more derivatives of glutamine-N,N-diacetic acid which have been prepared by reacting corresponding 2-alkyl- or 2-alkenylglycines or 2-alkyl- or 2-alkenylglycine nitriles or double glycines of the formula

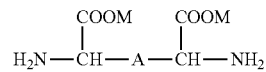

or double glycine nitriles of the formula

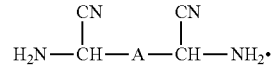

with formaldehyde and hydrogen cyanide or alkali metal cyanide or
iminodiacetic acid or iminodiacetonitrile with corresponding monoaldehydes or dialdehydes of the formula OHC-A-CHO and hydrogen cyanide or alkali metal cyanide and then hydrolyzing any nitrile groups still present to give carboxyl groups.

The aqueous solution is preferably used at a temperature in the range between 20 and 90°.

The aqueous solution comprising one or more derivatives of glycine-N,N-diacetic acid and/or one or more derivatives of glutamine-N,N-diacetic acid is introduced in a first process step into an evaporator with rotating internals, where it is concentrated to a crystal slurry with a solids concentration in the range from 60 to 85% by weight.

According to the invention, the rotating internals brush over the inside wall of the evaporator at a very small distance of less than or equal to 1% of the diameter of the evaporator. The very small distance between the rotating internals and the inside wall of the evaporator brings about a high shear rate in the liquid film on the inside wall of the evaporator. As a result, intrinsic crystal seed formation is initiated.

In a preferred embodiment, the rotating internals are positioned such that they scratch on the inside wall of the evaporator.

The evaporation in the first process stage takes place in particular in a temperature range between 50 and 140° C., preferably between 80 and 110° C. and in a pressure range between 0.1 bar absolute and 4 bar absolute, preferably in a pressure range between 0.8 bar absolute and 1.2 bar absolute. The elevated temperature in the first process stage is ensured in particular by heating the walls of the evaporation apparatus used with formation of a jacket through which a heat carrier circulates.

The evaporator used in the first process step is preferably a Sambay® evaporator. Sambay® evaporators are special thin-film evaporators with a central core pipe onto which movable wiper blades are arranged. As a result of the centrifugal force, these are pressed onto the heated wall of the evaporator. By varying the wiper blade type and thus the contact pressure, this evaporator can be optimally adapted to many problems. At a low rotor speed, it permits a high evaporation ratio for simultaneously very small amounts of discharge and is primarily suitable for the processing of products which form deposits. The Sambay® evaporator works at viscosities up to ca. 35 000 mPas.

The crystal slurry resulting after the first process step is then left to ripen by passing it to suitable apparatuses which provide an adequate residence time of at least 15 minutes, preferably between 15 minutes and 1 hour, or else between 15 minutes and 3 hours.

For this, the crystal slurry from the first process step is firstly passed to a paste bunker which is preferably equipped with stirring elements for thoroughly mixing the paste-like crystal slurry. Additionally, a fine powder fraction with average particle diameters of ≤200 μm can be introduced into the paste bunker and mixed with the crystal slurry, preferably in a fraction of up to 50%, based on the total weight of the substances introduced into the paste bunker. Consequently, fines fractions which are produced in the overall process can be utilized at this point.

The crystal slurry with optionally admixed fine powder is then passed to a thin-film contact dryer where, during a contact time of from about 0.5 to 20 minutes, in particular of about 10 minutes, and at a temperature in the range from about 60-140° C., the water content of the solids mixture is adjusted such that at the product exit from the thin-film contact dryer a powder is obtained which predominantly has the crystal modification of the monohydrate or of the dihydrate of MGDA.

The thin-film contact dryers used are, for example, high-speed paddle dryers from various manufacturers, for example Turbodryer from Vomm, horizontal thin-film dryers from Buss, short-path evaporators from 3V Cogeim or horizontal centrifugal dryer-reactors from VRV.

The product obtained from the thin-film contact dryer is characterized by better flowability, lower hygroscopicity and better storage stability compared with powders which have been prepared by known drying processes, for example by spray-drying or by the mixer-kneader process.

The invention also provides methylglycine-N,N-diacetic acid trisodium salt powder with a degree of crystallinity of ≥30% comprising a first crystalline modification with the d values in angstroms given below at the diffraction angles 2-theta in °:

| 2-theta (°) | d value (angstroms) |
| --- | --- |
| 8.4 | 10.5 |
| 9.5 | 9.3 |
| 11.1 | 8.0 |
| 13.2 | 6.7 |
| 13.9 | 6.35 |
| 15.8 | 5.6 |
| 16.5 | 5.36 |
| 16.84 | 5.26 |
| 17.34 | 5.11 |

-continued

| 2-theta (°) | d value (angstroms) |
| --- | --- |
| 17.67 | 5.02 |
| 18.92 | 4.69 |
| 20.29 | 4.37 |
| 21.71 | 4.09 |
| 22.3 | 3.98 |
| 23.09 | 3.85 |
| 24.74 | 3.59 |
| 25.36 | 3.51 |
| 27.04 | 3.29 |
| 28.28 | 3.15 |
| 29.63 | 3.01 |
| 30.09 | 2.97 | and/or a second crystalline modification with the d values in angstroms at the respective diffraction angles 2-theta in ° in the powder diffractogram corresponding to the table below:

| 2-theta (°) | d value (angstroms) |
| --- | --- |
| 8.2 | 10.80 |
| 10.5 | 8.40 |
| 15.55 | 5.70 |
| 16.47 | 5.38 |
| 17.09 | 5.18 |
| 18.10 | 4.90 |
| 18.82 | 4.71 |
| 21.00 | 4.23 |
| 21.35 | 4.16 |
| 22.64 | 3.92 |
| 23.69 | 3.75 |
| 24.73 | 3.60 |
| 26.75 | 3.33 |
| 28.93 | 3.08 |
| 29.88 | 2.99 |
| 31.46 | 2.84 |
| 31.88 | 2.80 |

The invention is illustrated in more detail below by reference to examples and also a drawing.

EXAMPLE 1

(For Comparison) Spray Drying

A quantitative stream of 60 kg/h of an aqueous solution of MGDA with a solids content of 40% was evaporated in a plate heat exchanger evaporator (heating area 1.7 m²) to a solids content of 59% and separated in a separating container. The evaporation is carried out at a wall temperature of 152° C. (steam heating) and at a pressure of 2.5 bar abs in the separator.

The evaporated solution was metered into the downstream piston membrane pump at a temperature of ca. 128° C. using a gear pump and sprayed into a spray tower using a single-material jet.

The spray tower had a diameter of 800 mm and a length of 12 m. The spray tower was operated with a quantity of air of 1400 kg/h and a gas inlet temperature of 160° C. The product outlet temperature was 127° C. and the solids content of the dry product 94.1%. The product was separated out via a 2-point discharge (directly at the spray tower and at the downstream filter).

The product prepared in this way was a pourable powder. The bulk density was 529 kg/m³. X-Ray structural analysis shows that the product is amorphous.

The storage behavior of this sample was evaluated in a desiccator test. For this, a 3 g sample is stored in an open weighing cup in a desiccator at 20° C. and a relative atmospheric humidity of 76% over a period of 144 hours. The mass increase of the sample is then ascertained and the pourability of the sample is evaluated. The mass increase was 27.1% and the sample had started to dissolve, i.e. it was wet and no longer pourable.

EXAMPLE 2

(For Comparison) Mixer-Kneader Process

A quantitative stream of 20.5 kg/h of an aqueous solution of MGDA with a solids content of 40% was preheated in a plate heat exchanger (heating area 1.7 m$^2$) to a solution temperature of 80° C. and metered into a CRP® 25 Conticontact dryer from List using a gear pump.

The List contact dryer is a twin-shaft apparatus with the internal dimensions 170*280 mm, a volume of 31 liters, a heating area of 1.3 m$^2$ and it was heated to a wall temperature of 174° C. by means of steam. The shafts were operated at speeds of 30 and 24 revolutions per minute. In this contact dryer the product was dried to a solids content of 92%.

The product prepared in this way was granules which were very easy to pour. The bulk density was ca. 650 kg/m$^3$. The X-ray powder diffractogram shows that the product has amorphous and crystalline fractions. The degree of crystallinity corresponding to the analysis described above is 30%.

The storage behavior of the sample was ascertained as described in example 1. The mass increase was 22.7% and the sample was slightly lumpy, i.e. it was no longer pourable, but could be converted to the pourable state again by gently tapping on the weighing cup.

EXAMPLE 3

(For Comparison) Mixer-Kneader Process

A quantitative stream of 32 kg/h of an aqueous solution of MGDA with a solids content of 40% was evaporated in a plate heat exchanger evaporator (heating area 1.7 m$^2$) to a solids content of 61.8% and metered into a DTB® 25 Conti contact dryer from List using a gear pump via a pressure retention valve. The evaporation was carried out at a wall temperature of 142° C. at the evaporator and at a pressure of 2.5 bar abs. in the separating container.

The List DTB 25 Conti contact dryer is a single-shaft apparatus with an internal diameter of 170 mm, a volume of 30 liters and a heating area of 1.2 m$^2$. It was heated to a wall temperature of 186° C. by means of steam. The shaft was operated at a speed of 16 revolutions per minute. In this contact dryer the product was dried to a solids content of 88.1%.

The product prepared in this way was very readily pourable granules. The bulk density was ca. 600 kg/m$^3$. The X-ray powder diffractogram shows that the product has amorphous and crystalline fractions. The degree of crystallinity corresponding to the analysis described above is 27%.

The storage behavior of the example was ascertained as described in example 1. The mass increase was 21.7% and the sample was slightly lumpy, i.e. it was no longer pourable, but could be converted to the pourable state again by gently tapping on the weighing cup.

EXAMPLE 4

Invention

A quantitative stream of 3.3 kg/h of an aqueous solution of MGDA with a solids content of 45.8% was evaporated in a laboratory Sambay® evaporator (heating area 0.046 m$^2$) to a solids content of 65.9%. Evaporation was carried out at a wall temperature of 205° C. at atmospheric pressure.

The evaporated solution was collected at a temperature of ca. 100° C. in a metering bunker with a capacity of 8 liters and cooled with stirring. The product was conveyed from this metering bunker by means of a metering screw into a rapidly rotating contact dryer.

The contact dryer had a diameter of 134 mm and a heating area of 0.166 m$^2$ and was heated to a wall temperature of 184° C. by means of steam. It was operated at a speed of 276 revolutions per minute. In this contact dryer the product was dried from a solids content of 65.9% to a solids content of 91.6%.

The product prepared in this way was readily pourable granules. The bulk density was 548 kg/m$^3$. The X-ray powder diffractogram shows that the product is crystalline. The degree of crystallinity corresponding to the analysis described above is 39%. The storage behavior of the sample was ascertained as described in example 1. The mass increase was 20.3% and the sample was still as pourable as during the initial weighing.

EXAMPLE 5

Invention

A quantitative stream of 3.2 kg/h of an aqueous solution of MGDA with a solids content of 45.5% was evaporated in a laboratory Sambay® evaporator (heating area 0.046 m$^2$) to a solids content of ca. 69%. The evaporation was carried out at a wall temperature of 120° C. at a reduced pressure of 0.5 bar.

The evaporated solution was collected at a temperature of ca. 80° C. in a metering bunker with a capacity of 8 liters and cooled with stirring. The product was conveyed from the metering bunker by means of a metering screw to a rapidly rotating contact dryer.

The contact dryer had a diameter of 134 mm and a heating area of 0.166 m$^2$ and was heated to a wall temperature of 120° C. by means of steam. It was operated at a speed of 275 revolutions per minute. In this contact dryer the product was dried from a solids content of 69% to a solids content of 88%.

The product prepared in this way was readily pourable granules. The bulk density was 555 kg/m$^3$. The X-ray powder diffractogram shows that the product is crystalline. The degree of crystallinity corresponding to the analysis described above is 58% of modification 1.

The storage behavior of the sample was ascertained as described in example 1. The mass increase was 18% and the sample was still as pourable as during the initial weighing.

Figure 4:
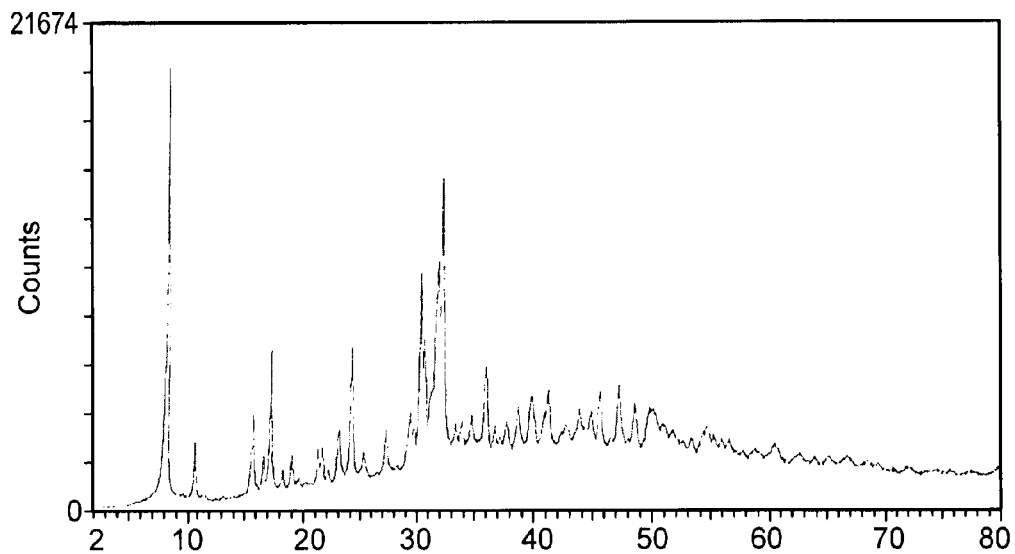
Figure 5:
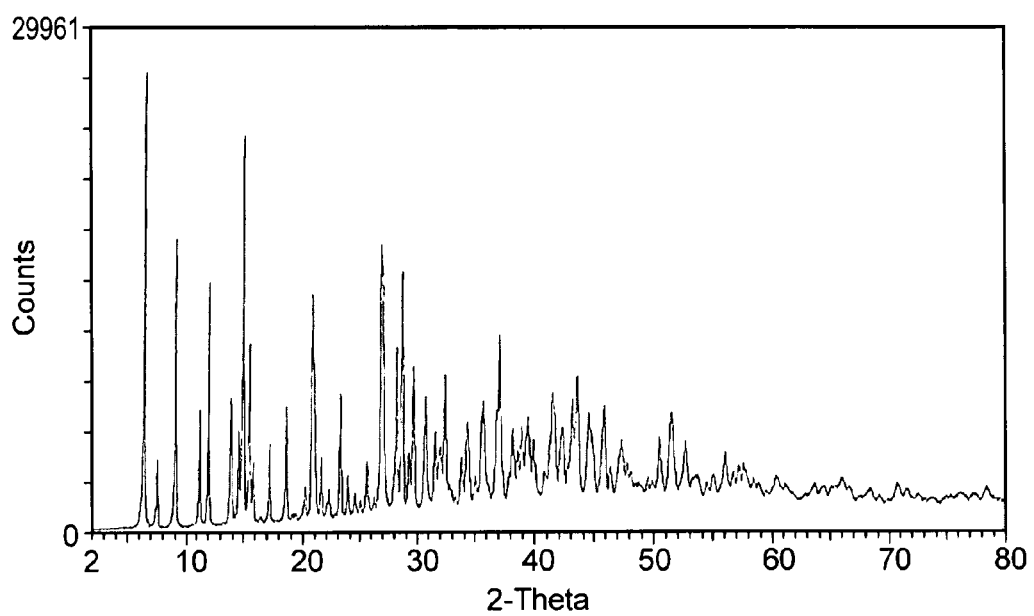

FIGS. 1 to 5 show X-ray powder diffractograms for the powders obtained according to examples 1 to 5 and show the increased degrees of crystallinity for powders obtained by the process according to the invention (FIGS. 4 and 5).

In the figures, the diffraction angle 2-theta, in °, is given on the abscissa, and the measured intensity, in counts (pulses) (dimensionless), is given on the ordinate.

The X-ray powder diffractometer measurements were carried out on a D8 Advance® diffractometer from Bruker AXS (Karlsruhe). In reflection with Cu—K α-radiation was measured with a variable diaphragm adjustment on the primary side and on the secondary side. The measurement range was 2° to 80° 2-theta, the step width 0.01° and the measurement time per angle step 3.6 seconds.

The degree of crystallinity was ascertained from the X-ray powder diffractograms in a known manner by, as usual, determining the surface fraction of the crystalline phase and of the amorphous phase and using these to calculate the degree of crystallinity, CD, as the ratio of the area of the crystalline phase, $I_c$, to the total area, consisting of the area of the amorphous phase, $I_a$, and the area of the crystalline phase, $I_c$:

$$CD=I_c/(I_c+I_a).$$

The determination of the degree of crystallinity can be carried out in particular using a software program, for example the software program TOPAS® from Bruker AXS.

For this, firstly an amorphous sample is measured and the linear course is fitted in a profile fit with the help of six individual lines. The line positions of these lines and their half-widths are then fixed and these values are saved as "amorphous phase".

For the sample to be measured for which the degree of crystallinity is to be determined, the surface fraction of the crystalline phase and the surface fraction of the amorphous phase is then determined and the degree of crystallinity CD is calculated therefrom in accordance with the formula given above.

The amorphous phase is used as defined above.

The crystalline phase can likewise be defined via its individual line positions analogously to the amorphous phase, or by reference to the following lattice constants, as so-called (hkl) phase (a=33.63, b=11.36 and c=6.20 and space group Pbcm), where the lattice parameters are variables which can be freely refined. The background is fitted as polynomial of the 1st degree.

The program TOPAS® calculates the optimal fit between measured diffractogram and the theoretical diffractogram consisting of amorphous and crystalline phase.

The invention claimed is:

1. A process for preparation of a powder, the powder comprising: at least one derivative of glycine-N,N-diacetic acid, at least one derivative of glutamine-N,N-diacetic acid, or a mixture thereof with a degree of crystallinity of ≥30%,
    the process comprising:
    concentrating an aqueous solution to obtain a crystal slurry, wherein the aqueous solution comprises the at least one derivative of glycine-N,N-diacetic acid, the at least one derivative of glutamine-N,N-diacetic acid, or the mixture thereof in a concentration range from 20 to 60% by weight, based on a total weight of the aqueous solution, and wherein the crystal slurry has a solids concentration of from 60 to 85% by weight, based on a total weight of the crystal slurry, and
    ripening the crystal slurry in a paste bunker and then in a thin-film contact dryer,
    wherein a residence time in the paste bunker and in the thin-film contact dryer is in total ≥15 minutes, and
    the concentrating occurs in an evaporator with rotating internals, which are arranged at a distance relative to an inside wall of the evaporator of ≤1% of a diameter of the evaporator.

2. The process of claim 1, wherein the rotating internals scratch on the inside wall of the evaporator.

3. The process of claim 1, wherein the aqueous solution comprises at least one alkali metal salt of methylglycine-N,N-diacetic acid as a derivative of glycine-N,N-diacetic acid.

4. The process of claim 1, wherein the aqueous solution comprises the at least one derivative of glycine-N,N-diacetic acid, the at least one derivative of glutamine-N,N-diacetic acid, or the mixture thereof in each case in a purity of ≥84%, based on the dry mass.

5. The process of claim 4, wherein the at least one derivative of glycine-N,N diacetic acid, the at least one derivative of glutamine-N,N diacetic acid, or the mixture thereof is prepared in a process selected from the group of processes consisting of:
    reacting corresponding 2-alkyl- or 2-alkenylglycine or 2-alkyl- or 2-alkenylglycine nitrile or double glycine of the formula

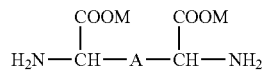

or double glycine nitrile of the formula

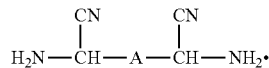

with formaldehyde and hydrogen cyanide or alkali metal cyanide; and
    reacting iminodiacetic acid or iminodiacetonitrile with a corresponding monoaldehyde or dialdehyde of the formula OHC-A-CHO and hydrogen cyanide or alkali metal cyanide, and then
    hydrolyzing any nitrile group still present to give a carboxyl group;
    wherein A is a $C_1$ to $C_{12}$ alkylene bridge or a chemical bond, and
    M is H, an alkali metal, an alkali earth metal, ammonium, or substituted ammonium, in appropriate stoichiometric quantities.

6. The process of claim 1, wherein the aqueous solution is introduced into the evaporator at a temperature of from 20 to 90° C.

7. The process of claim 1, wherein the evaporator is a thin-film evaporator having a central core pipe comprising a movable wiper blade.

8. The process of claim 1, wherein a sum of residence times in the paste bunker and in the thin-film contact dryer is in total from 15 minutes to 3 hours.

9. The process of claim 1, wherein the concentrating occurs at a temperature of from 50-140° C. and at a pressure of from 0.1-4 bar absolute.

10. The process of claim 1, wherein, the ripening in the paste bunker is in the presence of up to 50% by weight of fine powder with an average particle size of ≤200 μm, based on the total weight of the crystal slurry and of the fine powder.

11. The process of claim 1, wherein the ripening in the thin-film contact dryer is at a temperature of from 60 to 140° C.

12. The process of claim 8, wherein a sum of residence times in the paste bunker and in the thin-film contact dryer is from 15 minutes to 1 hour.

13. The process of claim 9, wherein the concentration occurs at a temperature in the range from 80-110° C., and a pressure of 0.8-1.2 bar absolute.

* * * * *